United States Patent
Tomiyama et al.

[11] Patent Number: 5,818,958
[45] Date of Patent: Oct. 6, 1998

[54] WIRE BEND INSPECTION METHOD AND APPARATUS

[75] Inventors: Hiromi Tomiyama; Takeyuki Nakagawa, both of Tokyo, Japan; Naoki Kanayama, San Jose, Calif.

[73] Assignees: Kabushiki Kaisha Shinkawa, Tokyo, Japan; Shinkawa U.S.A., Inc., Santa Clara, Calif.

[21] Appl. No.: 758,204

[22] Filed: Nov. 25, 1996

Related U.S. Application Data

[63] Continuation of Ser. No. 466,406, Jun. 6, 1995, abandoned.

[30] Foreign Application Priority Data

Oct. 14, 1994 [JP] Japan ................................. 6-276013

[51] Int. Cl.$^6$ ........................... G06K 9/00; G01N 21/00; H01L 23/48
[52] U.S. Cl. ..................... 382/145; 250/559.34; 257/784; 348/126
[58] Field of Search ..................... 382/145, 146, 382/147, 148, 149, 151; 348/126

[56] References Cited

U.S. PATENT DOCUMENTS

| | | | |
|---|---|---|---|
| 5,119,436 | 6/1992 | Holdgrafer | 382/146 |
| 5,138,180 | 8/1992 | Yamanaka | 356/604 |
| 5,396,334 | 3/1995 | Sugawara | 356/394 |
| 5,412,477 | 5/1995 | Kida | 356/394 |
| 5,485,398 | 1/1996 | Yamazaki et al. | 382/146 |
| 5,490,084 | 2/1996 | Okubo et al. | 382/145 |
| 5,563,703 | 10/1996 | Lebeau et al. | 356/237 |
| 5,627,912 | 5/1997 | Matsumoto | 382/146 |

FOREIGN PATENT DOCUMENTS

| | | | |
|---|---|---|---|
| 60-0008706 | 1/1985 | Japan | 382/146 |
| 4-330757 | 11/1992 | Japan | H01L 21/66 |
| 5-160233 | 6/1993 | Japan | H01L 21/66 |

*Primary Examiner*—Joseph Mancuso
*Assistant Examiner*—Jayanti K. Patel
*Attorney, Agent, or Firm*—Koda & Androlia

[57] ABSTRACT

A method and apparatus for inspecting bends in wires bonded between, for instance, pads of semiconductor chips and leads of lead frames using detection ranges established within imaging ranges in which images of bends are taken. Imaging range areas are established by dividing the distance between a first bonding point and a second bonding point of a target wire by the width of the detection range, and the wire bend is then detected in the respective imaging range areas.

4 Claims, 4 Drawing Sheets

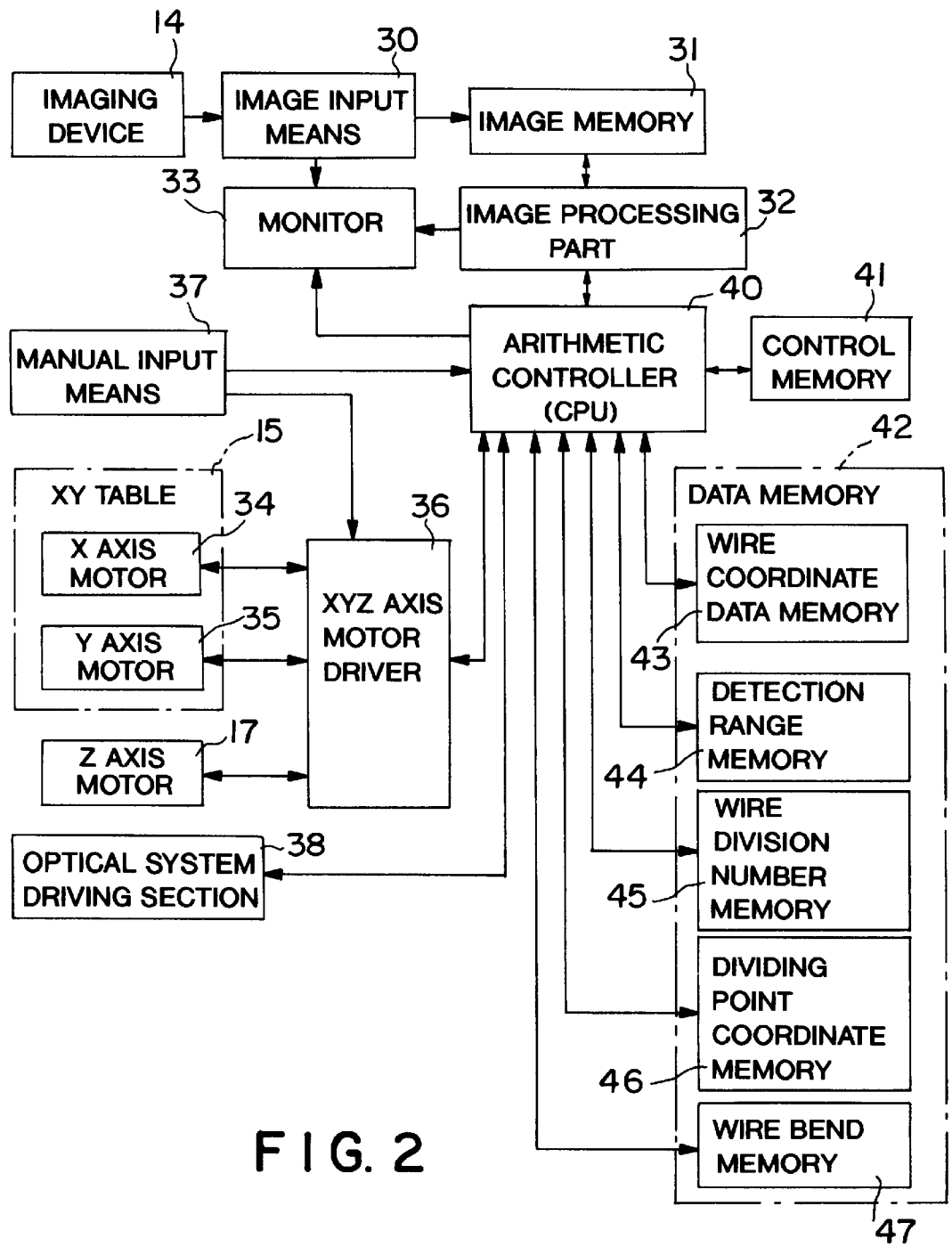
F I G. 2

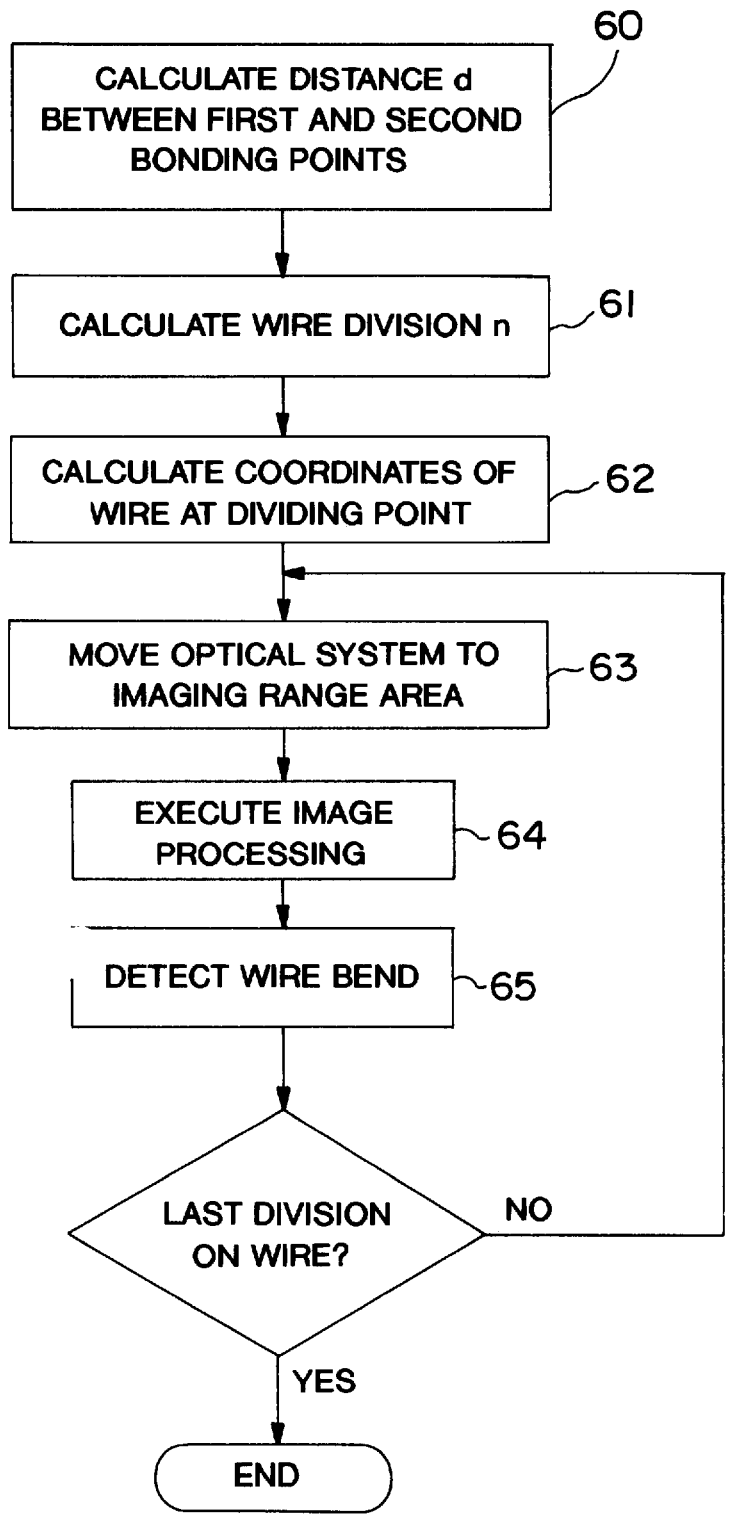
F I G. 3

WIRE BEND INSPECTION METHOD AND APPARATUS

This is a continuation of application Ser. No. 08/466,406, filed Jun. 6, 1995 now abandoned.

BACKGROUND OF THE INVENTION

1. Field of the Invention

The present invention relates to a method and apparatus for inspecting the bends in bonded wires in, for example, semiconductor devices.

2. Prior Art

Japanese Patent Application Laid-Open (Kokai) Nos. 4-330757 and 5-160233 are examples of conventional methods and apparatuses for inspecting bonded wires in semiconductor devices.

FIG. 4 illustrates the inspection apparatus of the prior art.

A workpiece 6 on which wires 5 have been bonded for connecting the pads 2 of a semiconductor chip 1 with the leads 4 of a lead frame 3 is placed on an inspection stand 10.

An illuminating means 11 is installed so as to be positioned above the workpiece 6 that is on the inspection stand 10. The illuminating means 11 is attached to the lower part of an optical system 12, and an imaging device 14 such as a CCD (photoelectric transducer element) camera is attached to the upper part of the optical system 12 via a diaphragm means 13. The optical system 12 to which the illuminating means 11 and imaging device 14 are attached is mounted in a vertically movable fashion to a supporting block 16 which is provided on an XY table 15. The optical system 12 is raised and lowered by a Z-axis motor 17.

With this apparatus, as shown in FIG. 5, the distance S is measured from a straight line 18 connecting the first bonding point 5a (which is a bonding point on the corresponding pad 2) of each wire 5 and the second bonding point 5b (which is a bonding point on the corresponding lead 4) of the wire 5, thus obtaining the bend in the wire 5.

In recent years, semiconductor devices have become larger and made with increased density. As a result, some products need the wires (i.e., the length of the wires 5) to be as long as 8 mm. Accordingly, the wire inspection devices inspect wires of a variety of lengths ranging from approximately 1 mm to 8 mm.

In the following description, wires of a length within a range to be imaged are referred to as "conventional wires", and wires of a length that exceeds the imaging range are referred to as "long wires".

When an inspection is made for an entire wire, it is possible to make an image of the conventional wire in its entirety, but it is impossible to take an image of the entire long wire if the magnification of an optical system is the same. Therefore, bends in the long wires are detected by lowering the magnification ratio of the optical system so that the entire wire is set in the imaging range or by inspecting partial images of the long wire without changing the magnification.

However, these prior art methods for taking images of the bonded wires have several problems. When the entire wire is inspected by changing the magnification ratio of an optical system, the precision of detection changes due to the change in the resolution of the image. In other words, in the detection of the long wires, the resolution becomes poor, and the precision of detection becomes inferior. In the case of methods in which partial images of the long wires are inspected, the bends of the overall wire, i.e., the wire track or shape, cannot be calculated.

SUMMARY OF THE INVENTION

Accordingly, the object of the present invention is to provide a wire bend inspection method and apparatus which can detect, regardless of the length of the wire, the bend of each wire as a whole under the same conditions, in other words, without altering the magnification ratio of optical systems.

The object is accomplished by unique steps provided by the present invention used in a method for inspecting the bends in wires bonded between the pads of a semiconductor chip and the leads of a lead frame by taking images of the wire bends with the use of an imaging device through an optical system, and the unique steps of the present invention comprise a step of setting detection ranges within an imaging range, a step of dividing the longer one of X and Y directional components of a distance between first and second bonding points of each wire imaged within the detection range so as to establish a multiple number of imaging range areas, and a step of detecting the wire bend in each of these imaging range areas.

The object of the present invention is also accomplished by a unique structure for a bonding wire bend inspection apparatus in which the bends in bonding wires bonded between the pads of a semiconductor chip and the leads of a lead frame are inspected by taking images of the wire bends using an imaging device via an optical system, and the unique structure of the present invention is that the apparatus includes a wire coordinate data memory which stores XY coordinates of each wire to be inspected, a detection range memory which stores the detection range set within the imaging range, a wire division number memory which stores the number of wire divisions obtained from the division of the longer one of the X and Y directional components of the distance between the first bonding point and second bonding point of each wire imaged in the detection range, a dividing point coordinate memory which stores the coordinates of the dividing points, a wire bend memory which stores the results of the wire bend inspection, and an arithmetic control unit which calculates the number of wire divisions and detects the wire bends by processing the images obtained as a result of taking images of the respective divided imaging range areas by the imaging device.

In the method and apparatus of the present invention, a detection range is set within the imaging range, a multiple number of imaging range areas are set by dividing the distance between the first and second bonding points of the wire in the detection range, and then the wire bend in each of the imaging range areas is detected. Accordingly, each wire can be detected as a whole always under the same conditions, without altering the magnification of the optical system, regardless of the length of the wire to be detected.

BRIEF DESCRIPTION OF THE DRAWINGS

FIG. 2 is a block diagram which illustrates one embodiment of the control circuit of the wire bend inspection apparatus of the present invention;

FIG. 3 is a flow chart of the operation of the present invention;

DETAILED DESCRIPTION OF THE INVENTION

One embodiment of the present invention will be described below with reference to FIGS. 1 through 4. In this embodiment, inspection is performed using the inspection apparatus shown in FIG. 4.

Figure 1A:
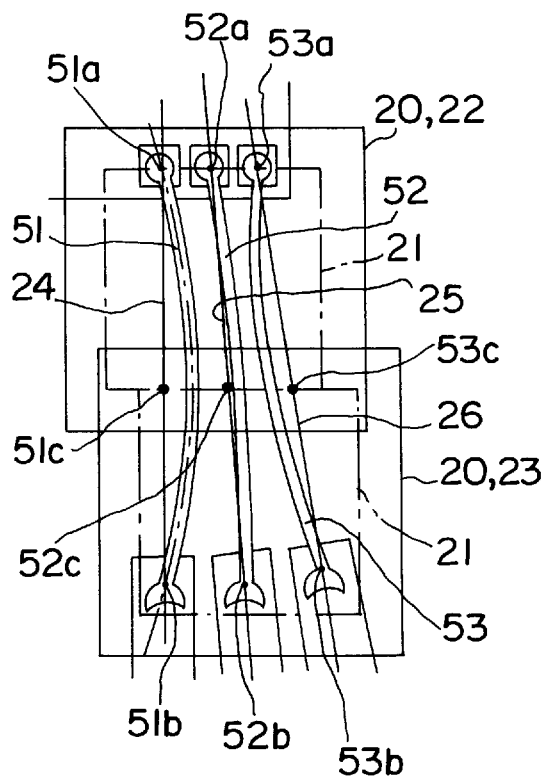
FIGS. 1(a), 1(b) and 1(c) are explanatory diagrams which illustrate one embodiment of the wire bend inspection method of the present invention.

As shown in FIG. 1(a), detection ranges 21 are set within imaging ranges 20.

Then, the longer one of the X and Y directional components of the distance between the first bonding points 51a (which is on, for example, a lead of a lead frame, not shown) and second bonding point 51b (which is on, for example, a pad of a chip, not shown) of a wire 51 to be imaged is divided by the width of the detection range 21. The number of ends obtained by the division is raised to a unit and taken as the number of wire divisions.

In the case of the wire 51 shown in FIG. 1, the wire 51 extends in the Y direction. Accordingly, the distance in this Y direction is divided by the width of the detection range 21 in the Y direction. If the wire 51 extends in the X direction, the distance in the X direction would be divided by the width of the detection range 21 in the X direction. If the wire 51 to be inspected extends at a 45-degree angle, then either the X or Y directional component of the distance of the wire 51 may be divided by the width of the detection range 21 in the X or Y direction.

The above relationship may be expressed by Formula 1, wherein D is the width of the detection range 21, d is a Y-direction component of the distance between the first bonding point 51a and second bonding point 51b, and n is the number of wire divisions.

Formula 1

$$n \geq d/D \quad (n: 1, 2, \ldots)$$

In FIG. 1(a), the number of wire divisions n is "2". In other words, the wire 51 is divided into two imaging range areas, i.e., first and second imaging range areas 22 and 23, and the bend in the wire 51 in each of the first and second imaging range areas 22 and 23 is detected.

First, the coordinates of the dividing point 51c where the first imaging range area 22 and second imaging range area 23 overlap are set on a straight line 24 that is drawn between the first bonding point 51a and second bonding point 51b.

Figure 1B:
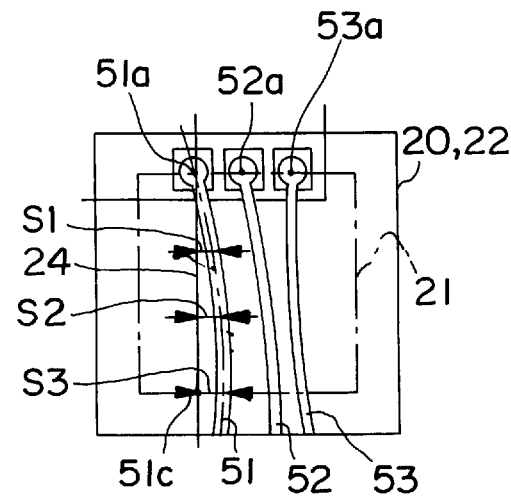
Figure 4:
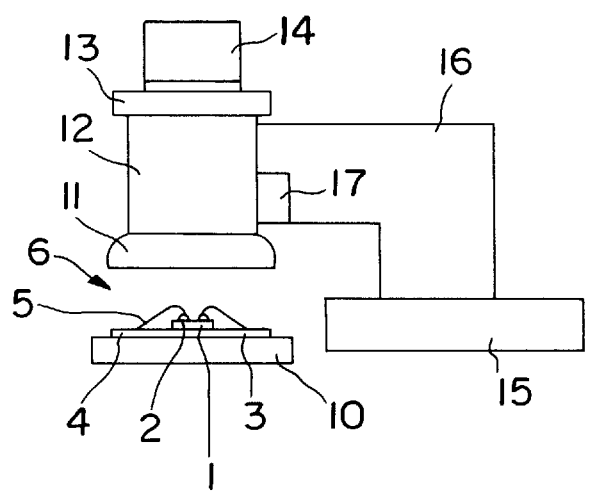
FIG. 4 is a schematic side view of a bonding wire inspection apparatus of the prior art.
Figure 5:
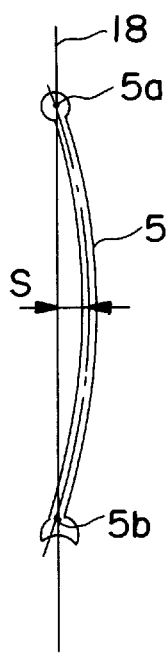
FIG. 5 is an explanatory diagram of a bonded wire to be inspected by the apparatus of FIG. 4.

Then, in a first stage, as shown in FIG. 1(b), the wire bend values S1, S2 and S3, are detected, moving from the first bonding point 51a toward the dividing point 51c in the first imaging range area 22 by means of the wire inspection apparatus as shown in FIG. 4.

Figure 1C:
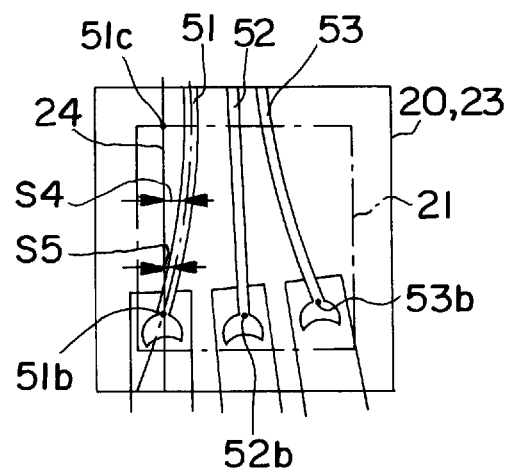

Next, in the second stage, the wire bend values S4 and S5, as shown in FIG. 1(c) are detected, moving from the dividing point 51c toward the second bonding point 51b in the second imaging range area 23 by means of the wire inspection apparatus as shown in FIG. 4.

Then, the wire bend from the first bonding point 51a to the second bonding point 51b, i.e., the track of the wire as a whole, is determined by combining the first-stage detection results and the second-stage detection results.

In cases where a multiple number of wires (in the present embodiment, three wires 51, 52 and 53) are to be imaged in the imaging range 20 (and not the wire 51 only) in the first- and second-stage detection, the wire bends of all of the wires 51, 52 and 53 are detected in the respective stages.

FIG. 2 shows one embodiment of the control circuit used in the wire inspection method illustrated in FIG. 1.

Images obtained by an imaging device 14 as shown in FIG. 4 are converted into digital signals by an image input means 30 and stored in an image memory 31. The image stored in this image memory 31 are subjected to image processing by an image processing part 32 and displayed on a monitor 33. An X-axis motor 34 and Y-axis motor 35 which drive the XY table 15 as shown in FIG. 4 together with a Z-axis motor 17 are controlled by an XYZ motor driver 36. This XYZ motor driver 36 is directly controlled by a manual input means 37 or by an arithmetic controller 40. Furthermore, the settings of an optical system driving section 38 for the diaphragm means 13 and illuminating means 11, etc. as shown in FIG. 4 are also controlled by the arithmetic controller 40.

The arithmetic controller 40 controls the processing and various parts of the system in accordance with a processing procedure stored in a control memory 41. In addition to controlling the XYZ motor driver 36 and optical system driver 38, the arithmetic controller 40 performs wire bend detection in accordance with images processed by the image processor 32, reads out and processes necessary data from a data memory 42, and stores calculated data in the data memory 42. The data memory 42 includes a wire coordinate data memory 43 which stores the XY coordinates of each wire 5 to be inspected, a detection range memory 44 which stores the detection range 21, a wire division number memory 45 which stores the number of wire divisions n, a dividing point coordinate memory 46 which stores the coordinates of the dividing point 51c, and a wire bend memory 47 which stores the wire bend inspection results.

The operation of the above embodiment will be described with reference to FIGS. 1 through 4.

When the workpiece 6 to which the wire 51 is bonded is set on the inspection stand 10, the distance d of the longer one of the X and Y directional components of the distance between the first bonding point 51a and second bonding point 51b is, as shown in FIG. 3, calculated at step 60 from the coordinates of the first bonding point 51a and second bonding point 51b. The calculation at step 60 of this distance d is performed by the arithmetic unit 40 which reads out the coordinates of the first bonding point 51a and second bonding point 51b from the wire coordinate data memory 43.

Next, the arithmetic unit 40 divides the distance d by the width D of the detection range stored in the detection range memory 44 and thus calculates at step 61 the number of wire divisions n. This number of wire divisions n is stored in the wire division number memory 45. Furthermore, the arithmetic unit 40 calculates at step 62 the coordinates of the dividing point 51c where the first and second imaging range areas 22 and 23 overlap on a straight line 24 connecting the first bonding point 51a and second bonding point 51b and stores the coordinates of this dividing point 51c in the dividing point coordinate memory 46.

Then, the arithmetic unit 40 operates the X-axis motor 34 and Y-axis motor 35 via the XYZ motor driver 36 in accordance with a procedure stored in the control memory 41 and then causes the XY table 15 to move so that the optical system 12 is positioned at step 63 above the first imaging range area 22 that is to be inspected as shown in FIG. 1b.

Next, the arithmetic unit 40 detects at step 65 the wire bend from the straight line 24 of the wire 51 that is imaged by the imaging device 14 and subjected to an image processing at step 64 by the image processor 32. This detection by the arithmetic unit 40 is done at step 65 and proceeds from the first bonding point 51a toward the dividing point 51c. The arithmetic unit 40 then stores the wire bend values S1, S2 and S3 that are obtained as a result of the detection in the wire bend memory 47.

When three wires 51, 52 and 53 are to be simultaneously imaged in the first and second imaging range areas 22 and 23, the wire bends in the wires 52 and 53 are detected at step 64 in the same manner as in the inspection of the wire 51 only, and the results are stored in the wire bend memory 47.

The first stage is completed as described above.

Next, in the second stage, the arithmetic unit 40 actuates the X-axis motor 34 and Y-axis motor 35 via the XYZ motor driver 36, thus causing the XY table 15 to move so that the optical system 12 is positioned above the second imaging area 23 that is to be inspected as shown in FIG. 1(c). Then, as in the first stage, the bend from the straight line 24 of the wire 51 is detected at step 64 in such a manner that the detection proceeds from the dividing point 51c toward the second bonding point 51b. The wire bend values S4 and S5 obtained as a result of this detection are stored in the wire bend memory 47. The wire bends of the wires 52 and 53 are likewise detected and stored in the wire bend memory 47.

With the above operations, the second stage is completed.

The second-stage inspection results are combined with the corresponding first-stage inspection results for the wires 51, 52 and 53 and are stored in the wire bend memory 47. As a result, the wire bends from the first bonding point 51a, 52a and 53a to the second bonding point 51b, 52b and 53b, in other words the shape or track of the wire as a whole, is determined for each wire.

As seen from the above, a detection range 21 is set within the imaging range 20, first and second imaging range areas 22 and 23 are set by dividing the distance d of the longer one of the X and Y directional components of the distance between the first bonding point 51a, 52a or 53a and second bonding point 51b, 52b or 53b of each wire 51, 52 or 53 by the width of the detection range 21, and the bend from a straight line 24, 25 and 26 connecting the first bonding point 51a, 52a and 53a and second bonding point 51b, 52b and 53b is detected in the respective first and second imaging range areas 22 and 23. Thus, each wire can be detected as a whole under the same conditions. In other words, all of the wires are detected without altering the magnification ratio of the optical system 12, regardless of the length of the wire. Thus, wires ranging from conventional wires to long wires can be detected without any drop in precision.

As described above, according to the present invention, a detection range is set within an imaging range, a multiple number of imaging range areas are set by dividing the distance between the first and second bonding points of a wire in the detection range, and then the wire bend in each of the imaging range areas is detected. Accordingly, the bend of each wire as a whole is detected under the same conditions regardless of the length of the wire. Thus, the invention provides an improved precision of detection of bonded wires.

We claim:

1. A wire bend inspection method for inspecting bends in bonding wires bonded between pads of a semiconductor chip and leads of a lead frame by imaging said wire bends with an imaging device through an optical system, wherein said method comprises the steps of setting detection ranges for an X and Y direction within an imaging range, determining which of X and Y directional components of a distance between a first bonding point and a second bonding point of each of said wires imaged in said imaging range is longer, dividing said longer one of X and Y directional components of a distance between said first bonding point and said second bonding point of each of said wires imaged in said imaging range by a respective one of said detection ranges, rounding up the result of said division to a positive integer equal to or greater than 2, dividing said longer of said X and Y directional components of a distance between said first bonding point and said second bonding point of each of said wires imaged in said imaging range by said positive integer to establish a plurality of imaging range areas, and detecting a wire bend in each of said plurality of said imaging range areas whereby a bend of a wire which is larger in length than said imaging range can be inspected utilizing said plurality of imaging range areas without changing a magnification ratio of said optical system.

2. A wire bend inspection method according to claim 1, wherein for a plurality of wires to be inspected, a bend in a portion of all of said plurality of wires in a first imaging range area is inspected before inspecting a bend in portions of all of said plurality of wires in subsequent imaging range areas.

3. A wire bend inspection apparatus for inspecting bends in bonding wires bonded between pads of a semiconductor chip and leads of a lead frame by imaging said wire bends with an imaging device through an optical system, said apparatus comprising a wire coordinate data memory which stores XY coordinates of each wire to be inspected, a detection range memory which stores X and Y detection ranges set within an imaging range, a means for determining which one of X and Y directional components of a distance between first and second bonding points of each wire imaged in said imaging range is longer, a wire division number memory which stores a number of wire divisions obtained from a division of said longer one of X and Y directional components of a distance between said first and second bonding points of each wire imaged in said imaging range by a respective one of said X and Y detection ranges which is rounded up to a positive integer ≧2, a dividing point coordinate memory which stores coordinates of said dividing points of said wire division, a wire bend memory which stores a result of said wire bend inspection, and an arithmetic control unit which calculates a number of wire divisions by dividing said longer one of X and Y directional components of a distance between a first bonding point and a second bonding point of each of said wires imaged in said imaging range by said positive integer and detects wire bends by processing images obtained as a result of an imaging of respective divided imaging ranges areas by means of said imaging device whereby a bend of a wire which is larger in length than said imaging range can be inspected utilizing said divided imaging range areas without changing a magnification ratio of said optical system.

4. An apparatus according to claim 3, wherein for a plurality of wires to be inspected, a bend in a portion of all of said plurality of wires in a first of said divided imaging range areas is inspected before inspecting a bend in portions of all of said plurality of wires in subsequent divided imaging range areas.

* * * * *